United States Patent [19]

Bhatta et al.

[11] Patent Number: 5,254,115
[45] Date of Patent: Oct. 19, 1993

[54] COAGULATING SCALPELS

[75] Inventors: Krishna M. Bhatta, Brookline, Mass.; Thomas E. Haw, Portland, Oreg.

[73] Assignee: The General Hospital Corporation, Boston, Mass.

[21] Appl. No.: 775,171

[22] Filed: Oct. 11, 1991

Related U.S. Application Data

[63] Continuation-in-part of Ser. No. 595,448, Oct. 11, 1990, abandoned.

[51] Int. Cl.$^5$ .............................................. A61B 17/32
[52] U.S. Cl. ..................................... 606/16; 606/170; 606/167
[58] Field of Search ................................ 606/2, 10–17, 606/27–29, 33, 37–41, 45–52; 128/395, 399, 398

[56] References Cited

U.S. PATENT DOCUMENTS

| | | | |
|---|---|---|---|
| 3,865,113 | 2/1975 | Sharon et al. | 128/395 X |
| 4,211,229 | 7/1980 | Wurster | 128/395 X |
| 4,249,533 | 2/1981 | Komiya | 128/395 X |
| 5,026,370 | 6/1991 | Lottick | 606/49 X |
| 5,078,712 | 1/1992 | Easley et al. | 606/16 |

FOREIGN PATENT DOCUMENTS 3209444 10/1982 Fed. Rep. of Germany ........ 606/14

OTHER PUBLICATIONS

Podstata et al, Acta Universitatis Palackianae Olomucensis Facultatis Medicine 113:247–258, 1986.

*Primary Examiner*—Peter A. Aschenbrenner
*Attorney, Agent, or Firm*—Fish & Richardson

[57] ABSTRACT

A coagulating scalpel including a cutting and coagulating element and a dissecting element. The dissecting element and cutting and coagulating element is positioned and configured and of such size that tissue to be cut can pass over or along a surface of the dissecting element and into the cutting zone of the scalpel. The surface of the dissecting element is adapted to permit substantially free passage of the tissue over or along the surface of the dissecting element upon movement of the scalpel.

42 Claims, 3 Drawing Sheets

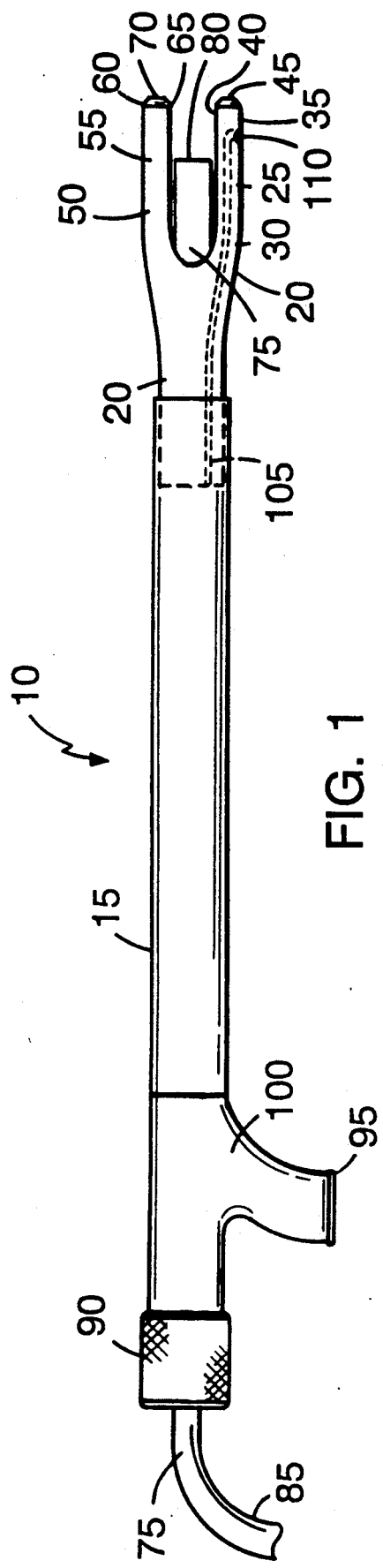
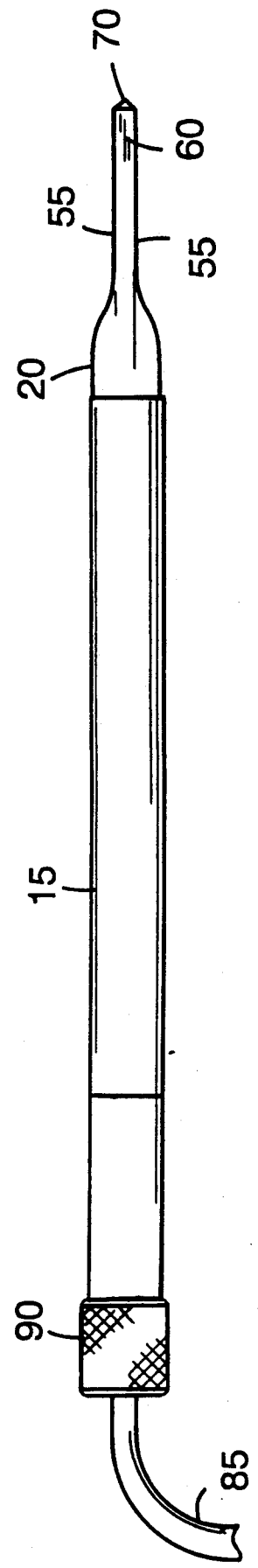

COAGULATING SCALPELS

This invention was made with Government support under Contract #N00014-86-K-0117 awarded by the Office of Naval Research. The Government has certain rights in this invention.

BACKGROUND OF THE INVENTION

This application is a continuation-in-part of U.S. Ser. No. 07/595,448, filed Oct. 11, 1990.

The invention relates to coagulating scalpels.

Laser scalpels simultaneously cut and coagulate tissue. One of the primary advantages of these instruments is that the flow of blood from cut tissue is very greatly reduced by heat induced coagulation in the tissue adjacent to the incision Reduction of the flow of blood, or hemostasis, is particularly important in endoscopic surgery.

Laser scalpels have taken a number of forms, reflecting e.g., efforts to combine laser coagulation with mechanical cutting, to adapt laser cutting to particular surgical procedures, and to direct or limit the path of the laser-induced incision. For example, Komiya U.S. Pat. No. 4,249,533 describes a laser knife including a laser radiation transmission member and a pair of elongate resilient strips to hold a target. Prozorov et al. U.S. Pat. No. 4,185,633 describes a laser surgery-apparatus which combines a mechanical cutting element and an adjacent structure for forming a laser beam support near the cutting element's edge. Sharon et al. U.S. Pat. No. 3,865,113 describes a laser device which includes a leg which extends beyond the distal end of the laser conduit. Auth et al. U.S. Pat. No. 4,126,136 describes a photocoagulating system including a scalpel having a sharp, transparent blade for forming an incision, and a laser optically coupled to the blade for coagulating the adjacent incision. Komiya U.S. Pat. No. 4,266,547 describes a laser knife suited for endoscopy including a laser radiation emitter located on one of a pair of holders, the holders adapted to hold an affected part sandwiched therebetween, and a laser radiation acceptor located on the other holder. Sunago et al., U.S. Pat. No. 4,492,230 describes an extension mechanism for a laser scalpel which extends beyond the tip of the scalpel and limits the depth of cutting.

SUMMARY OF THE INVENTION

The invention features a coagulating scalpel, preferably suitable, e.g., for endoscopic or hand held use, including a cutting and coagulating element and one or more dissecting element.

In preferred embodiments, a dissecting element (which includes a distal tip or end and which has a longitudinal axis) is disposed adjacent to the cutting and coagulating element, such that a line coaxial with the longitudinal axis of the cutting and coagulating element and extending beyond the tip of the cutting and coagulating element does not intersect the dissecting element. In other embodiments, the cutting and coagulating element and the dissecting element are disposed such that cutting radiation emitted from the distal tip of the cutting and coagulating element, and preferably from the face of the distal tip, is not completely obstructed, absorbed, or blocked by the dissecting element.

Other preferred embodiments include those in which: the cutting zone produced by the cutting and coagulating element is proximal to the distal tip of the dissecting means (preferably the dissecting means over which tissue to be cut passes) e.g., the cutting zone is between the distal tip of the cutting and coagulating means and the end of one or more (or all) of the dissecting elements; the cutting zone is adjacent the distal surface of the cutting and coagulating element; the cutting zone is at or near the surface of the distal tip of the cutting and coagulating element, i.e., it is within a distance equal to 1-10, preferably 1-5, more preferably 1-2 diameters of the cutting and coagulating element; the dissecting element and cutting and coagulating element are positioned and configured and of such size that tissue to be cut can pass over or along a surface of the dissecting element and into the cutting zone of the scalpel, wherein the surface of the dissecting element is adapted to permit substantially free passage of the tissue along or over the surface of the dissecting element upon movement e.g., forward movement of the scalpel; the dissecting element and cutting and coagulating elements are positioned and configured and of a size such that tissue to be cut, e.g., a blood vessel, or a planar or laminar structure, e.g., a membrane, an adhesion, or skin, can pass, e.g., slide, over or along a surface of the dissecting element and enter the cutting zone; the dissecting element and cutting and coagulating element are positioned and configured and of a size such that tissue to be cut which passes, e.g., slides, over or along a surface of the dissecting element and into the cutting zone, can be subjected, preferably simultaneously, to the action (e.g., heat) of the cutting and coagulating element and to mechanical force, e.g., compression or tension imparted by movement (e.g., movement away from, e.g., in a forward, (i.e., movement in the direction of the cut to be made in the tissue to be cut) upward, outward, lateral, or lifting direction, (with respect to the original position or conformation of the tissue cut or the tissue underlaying the tissue to be cut)), of the scalpel (or tissue) thereby allowing the cutting action of the cutting and coagulating element, e.g., heat, to be combined with mechanical cutting action, tension, pressure, or stretching applied to the tissue to be cut by the device, preferably allowing the tissue to be cut with less heat than would be needed to cut the tissue in the absence of the mechanical force; the dissecting element over or along which tissue to be cut passes is free of obstructions which would prevent substantially free passage of the tissue over or along the surface of the dissecting element into the cutting zone; the dissecting element and cutting and coagulating elements are positioned and configured such that the cutting zone is intersected by a line extending from the center of the distal tip of the cutting and coagulating element to the distal tip of the dissecting element; the distal end of one (or all) dissecting element extends (or can be positioned to extend) no more than about 30, preferably no more than about 15, more preferably no more than about 10, more preferably no more than about 5, and even more preferably no more than 1 millimeter beyond the distal end of the cutting and coagulating element or the cutting zone (in a particularly preferred embodiment the tip of the dissecting element extends 6-7 millimeters beyond the tip of the cutting and coagulating element); the distance, preferably the lateral distance, i.e., distance on a line perpendicular to the proximal-distal (or long) axis of the instrument, between the distal tip of the cutting and coagulating element or the cutting zone, and the surface of the dissecting element which faces the cutting and coagulating element, or cutting zone, and over or along which tissue to be cut passes is less than 600 microns, preferably less than 300 microns, more preferably less than 120 microns, more preferably less than 60 microns, and more preferably less than 10 microns (In a particularly preferred embodiment there is essentially no gap: the cutting and coagulating element lies adjacent and in contact with the dissecting element); the lateral distance between the outer surface (i.e., the surface opposite the surface which faces the cutting and coagulating element, or cutting zone) of the dissecting element (preferably the dissecting element over or along which tissue to be cut passes) and the center of the distal tip of the cutting and coagulating element or cutting zone, is less than about 5 millimeters, preferably less than about 2 millimeters, more preferably less than about 1 millimeter, and most preferably less than about 0.2 millimeters.

Preferred embodiments include those in which the cutting and coagulating element is an optical filament capable of transmitting laser light, an electrocautery element, a radio frequency cautery element, or an ultrasound element. Cutting and coagulating can result from cutting radiation from the cutting and coagulating means impinging on tissue, or, from tissue coming into contact with the cutting and coagulating element, preferably when the cutting and coagulating element is self-heated, e.g., by residual absorption of a laser beam.

The configuration of the cutting and coagulation elements and dissecting element differ in various preferred embodiments. For example, there are preferred embodiments wherein the distal end of the dissecting element (or elements) is flush with the distal end of the cutting and coagulating element (a configuration which is useful e.g., in blunt dissection), wherein the distal end of the dissecting element extends beyond the distal end of the cutting and coagulating element (a configuration which is useful e.g., in adhesiolysis), wherein the distal end of the cutting and coagulating element extends beyond the distal end of the dissecting element (which is useful e.g., in tissue vaporization), and wherein there is a gap between the cutting and coagulating element and the dissecting element. In preferred embodiments the cutting and coagulating element is slidably mounted with respect to the dissecting element so that the position of the distal tip of the cutting and coagulating element relative to the distal tip of the can be adjusted. The cutting and coagulating element can be locked in any of these (or intermediate) positions.

Preferred embodiments of the laser scalpel include those in which the dissecting element includes a sharp edge, a blunt edge, and/or cooling means e.g., refrigerating means e.g., a channel through which a coolant can be circulated or passed, within a dissecting element. Other preferred embodiments of the laser scalpel include means for removing unwanted material from the area of cutting and coagulating, e.g., aspiration means, and/or means for irrigating the area of cutting and coagulating with an irrigating solution. Aspiration or irrigation could be via channels leading through the dissecting element to ports on a surface of the dissecting element.

In yet other preferred embodiments the coagulating scalpel includes a first and a second or auxiliary dissecting element. Preferably the cutting and coagulating element is disposed in a gap between the first dissecting element and the second or auxiliary dissecting element. The width of the gap (measured laterally between the insides of the dissecting element (e.g., at the distal end of one of the elements)) is less than about 0.075 millimeters, preferably less than about 0.4 millimeters, more preferably less than about 0.8 millimeters, more preferably less than 4 millimeters, and more preferably less than about 8 millimeters. In preferred embodiments the distal tips of the first and second dissecting elements extend beyond the distal tip of the cutting and coagulating element forming a notch, with a plane perpendicular to the long axis of the scalpel passing through the distal face of the cutting and coagulating element forming the bottom of the notch and the dissecting elements forming the sides of the notch, the notch having a volume of no more than about 1, preferably no more than about 5, more preferably no more than about 7-8, more preferably no more than about 50, and yet more preferably of no more than about 100 cubic millimeters.

The coagulating scalpels of the invention can be used in surgical procedures, e.g., in endoscopic procedures, wherein a first structure is dissected, preferably with the dissecting element, from a second structure.

In another aspect, the invention features a surgical method for cutting a first biological structure laying adjacent a second biological structure. The method includes: providing a coagulating scalpel as described herein; hooking and lifting the first structure using a dissecting element of the scalpel; and activating the cutting and coagulating element to cut the first structure.

Preferred embodiments include those in which: the first, second, or both structures are subsequently cut, preferably with the cutting and coagulating element of a coagulating scalpel; the method further comprises moving the scalpel to impart mechanical force to the first structure; activation of the cutting and coagulating element an movement of the scalpel are performed simultaneously, thereby combining the action of the cutting and coagulating element, e.g., heat, with mechanical force, e.g., pressure, stretching, or tension, imparted to the tissue by movement of the scalpel; the first and/or second structure is a planar structure, e.g., a skin, an adhesive, or a membrane; the first structure is a membrane adjacent the gallbladder; the first and/or second structure is a hollow organ, e.g., the gallbladder; and less than about 10, preferably less than about 8, and more preferably less than about 6 watts of power are supplied to the cutting and coagulating device.

In another aspect the invention includes a method of separating a first structure from a second structure including, hooking and lifting the first structure with the dissecting element of a coagulating scalpel of the invention, and cutting the first structure with the cutting and coagulating element of the coagulating scalpel.

In preferred embodiments the method further includes moving the scalpel e.g., in the direction of a portion of the second structure to be cut, thereby combining the action of the cutting and coagulating element e.g., heat, with the mechanical force imparted by the movement; and less than about 10, preferably less than about 8, and more preferably less than about 6 watts of power are supplied to the cutting and coagulating device.

In another aspect, the invention features, a coagulating scalpel the distal end of which comprises a cutting and coagulating element, a first dissecting element, and a second dissecting element, the cutting and coagulating element being positioned in a gap between the first and the second dissecting elements, the scalpel having one or more of the following characteristics: the longitudinal axes of the first and second dissecting elements and the longitudinal axis of the portion of the cutting and coagulating element that lies adjacent the dissecting elements are essentially parallel; the distal tips of the first and second dissecting elements extend beyond the distal tip of the cutting and coagulating element forming a notch with a plane perpendicular to the long axis of the scalpel passing through the distal face of the cutting and coagulating element forming the bottom of the notch and the dissecting elements forming the sides of the notch; or, the distal tip of the scalpel is essentially spatulate in shape.

Preferred embodiments include those in which: the notch has a volume of no more than about 1, preferably no more than about 5, more preferably no more than about 7-8, more preferably no more than about 50, and yet more preferably of no more than about 100 cubic millimeters; the scalpel further includes means for adjusting the position of the distal end of the cutting and coagulating element relative to the distal end of the first (or second or both) dissecting elements; the distal end of one or both of the dissecting elements is flush with the distal end of the cutting and coagulating element; the distal end of the cutting and coagulating element extends beyond the distal end of one or both of the dissecting elements; the distal end of one or both of the dissecting elements extends beyond the distal end of the cutting and coagulating element; the distal end of one (or all) dissecting element extends (or can be positioned to extend) no more than about 30, preferably no more than about 15, more preferably no more than about 10, more preferably no more than about 5, and even more preferably no more than 1 millimeter beyond the distal end of the cutting and coagulating element or the cutting zone (in a particularly preferred embodiment the tip of the dissecting element extends 6-7 millimeters beyond the tip of the cutting and coagulating element); the lateral distance between the outer surface of the first dissecting element and the outer surface of the second dissecting element is less than about 10 millimeters, preferably less than about 4 millimeters, more preferably less than about 2 millimeters, and most preferably less than about 0.4 millimeters; the lateral distance of a gap (or notch, when measured, e.g., at the extreme distal end of a dissecting element) between the first and the second dissecting element is less than about 0.075 millimeters, preferably less than about 0.4 millimeters, more preferably less than about 0.8 millimeters, more preferably less than 4 millimeters, and more preferably less than about 8 millimeters; the cutting and coagulating element and the dissecting elements are disposed such that a line coaxial with the longitudinal axis of the cutting and coagulating element and extending beyond the distal tip of the cutting and coagulating element does not intersect either of the dissecting elements; the cutting and coagulating element is an optical filament capable of transmitting laser light; one of the dissecting element includes a sharp edge; one of the dissecting element includes a blunt edge; the scalpel includes means for cooling a dissecting element; the scalpel includes means for removing unwanted material from the area of cutting and coagulating; the scalpel includes means for irrigating the area of cutting and coagulating; the scalpel is adapted for endoscopic use; the surface of at least one of the dissecting elements is adapted to permit substantially free passage of the tissue along or over the surface of the dissecting element upon movement e.g., forward of the scalpel the dissecting element and cutting and coagulating element are positioned and configured and of a size such that tissue to be cut which passes, e.g., slides, over or along a surface of the dissecting element and into the cutting zone, can be subjected, preferably simultaneously, to the action (e.g., heat) of the cutting and coagulating element and to mechanical force, e.g., compression or tension imparted by movement (e.g., movement away from, e.g., in a forward, (i.e., movement in the direction of the cut to be made in the tissue to be cut) upward, outward, lateral, or lifting direction, (with respect to the original position or conformation of the tissue cut or the tissue underlaying the tissue to be cut)), of the scalpel (or tissue) thereby allowing the cutting action of the cutting and coagulating element, e.g., heat, to be combined with mechanical cutting action, tension, pressure, or stretching applied to the tissue to be cut by the device preferably allowing the tissue to be cut with less heat than would be needed to cut the tissue in the absence of the mechanical force.

In another aspect, the invention teaches, a surgical method for cutting a biological structure e.g., a planar structure, e.g., a membrane or adhesion including; providing a scalpel of the invention; engaging all or a portion of the structure in the gap or notch between the first and the second dissecting elements; moving the scalpel to impart mechanical force to the structure; and activating the cutting and coagulating element to cut the structure.

Preferred embodiments include those in which: the method further includes moving the scalpel in the direction in which the first structure is to be cut to impart the mechanical forces to the structure; the activation of the cutting and coagulating element and the movement are performed simultaneously, thereby combining the action of the cutting and coagulating element e.g., heat, with the mechanical force imparted by movement of the scalpel to cut tissue; the method is performed endoscopically; the structure is a membrane adjacent the gallbladder; less than 10, preferably less than 8, and more preferably less than 6 watts of power are supplied to the cutting and coagulating element.

In another aspect, the invention features a method of separating a first biological structure from a second biological structure including simultaneously applying to tissue joining the first and second structure heat and mechanical force, the heat, in combination with the mechanical force, being sufficient to seperate the first and second biological structure by parting the tissue. The heat is preferably produced by delivery of less than 10 watts, preferably less than 8 watts, and more preferably less than 6 watts, to the instrument transferring heat to the structure to be cut and, in any case, the amount of heat is less than the amount of heat which would be required to part the tissue in the absence of mechanical force.

The cutting and coagulating elements need not be powered during some phases of use, e.g., during some blunt dissections.

Cutting radiation, as used herein, means electromagnetic, heat, sound, or other energetic radiation that can cut and coagulate tissue.

Dissecting, as used herein refers to manipulating a structure, e.g., an anatomical feature or structure. This can include changing the position of the structure, e.g., changing its position relative to a second structure. Dissecting may, or may not, involve vaporizing, cutting, tearing, or other types of separation.

A coagulating and cutting element (or cutting and coagulating element), as used herein, is an element which cuts and coagulates tissue, including lasers, electrocautery element, ultrasound elements, and radio frequency cautery devices. Preferred lasers are those the emissions of which can be transmitted through an optical fiber or filament, e.g., a flexible fused silica or quartz fiber. $CO_2$ lasers, the emissions of which can not be transmitted through fibers, are less preferred.

Cutting zone, as used herein, refers to the zone in which cutting occurs. Preferably, the cutting zone is or includes: the region immediately adjacent the distal tip of the cutting and coagulating element; the focal point of the cutting and coagulating element; a region in which cutting occurs essentially upon entry into the zone; or a region in which cutting occurs essentially upon entering the zone if simultaneous mechanical force, e.g., tension is applied to the tissue to be cut. Adjustment of power settings, or the presence and amount of mechanical tension, can affect cutting zone size and shape.

Proximal, as used herein, refers to the end of the device (or end of a component of the device) nearest the operator. Distal, as used herein, refers to the end of the device (or end of a component of the device) nearest the patient. The distal end or tip of the cutting and coagulating element is the end nearest the patient and is the energy emitting end. The distal end or tip of the dissecting element is the end nearest the patient.

Devices and methods of the invention provide for the simultaneous application of heat, e.g., from a laser, and mechanical force to cut tissue with less heat than would be required to cut the same tissue in the absence of heat. This method of cutting, referred to as heat separation or heat-based separation, allows cutting of tissue with minimal tissue vaporization, charring, or other forms of thermal damage. Devices and methods of the invention allow surgical procedures to be performed easily, rapidly while minimizing the power, e.g., the power supplied to a laser cutting and coagulating element, used to cut tissue. For example, the combination of heat with mechanical pressure allows heat-based separations, as opposed to heat or light based vaporization, burning, or similar destruction of tissue. As compared to conventiional laser cutting, heat-based separation minimizes tissue loss (through for e.g., vaporization) and charring associated with surgical procedures.

The coagulating scalpels of the invention simultaneously cut and coagulate (thereby minimizing bleeding), facilitate both blunt and sharp dissections, and minimize thermal damage to tissue in the surgical field. The design of coagulating scalpels of the invention allows protection of the cutting and coagulating element, e.g., a laser filament, from damage, and reproduce the feel, in the hand of the surgeon, of a traditional steel scalpel. The ability to facilitate blunt and sharp dissections is particularly desirable in separating adhesions, e.g., when a first structure, e.g., a membrane, must be hooked and lifted away from a second underlying structure e.g., an organ, prior to cutting. The ease with which blunt and sharp dissections are performed result in reduced operation times.

The size, placement, and configuration of the cutting and coagulating element and the dissecting element allow the operator to lift or hook or otherwise engage, (e.g., in the fork or notch between two dissecting elements) a tissue with the dissecting element, slide the tissue over or along a surface of a dissecting element (e.g., by a slight motion of the instrument in the direction of the tissue) to bring the tissue into the cutting zone. By activating the cutting and coagulating element and lifting, pushing, or otherwise applying mechanical force, e.g., pressure, tension, or compression, to the tissue to be cut preferably in the direction the cut is to be made, the device allows the cutting action of the cutting and coagulating element, e.g., heat, to be combined with mechanical force applied to the tissue to be cut by the device. Thus, the effects of both the cutting and coagulatory element, and mechanical force, are combined to cut tissue.

Coagulating scalpels of the invention allow simultaneous effecting of blunt dissection (preferably made with the dissecting element) and sharp incisions (preferably made with the cutting and coagulating element), both in unzipping operations and in other procedures, e.g., in lifting and separating the gallbladder from its bed.

Other features and advantages of the invention will be apparent from the following description of the preferred embodiments, and from the claims.

DESCRIPTION OF THE PREFERRED EMBODIMENTS

The drawings will first be briefly described.

DRAWINGS

FIG. 1 is a not to scale side view of a laser scalpel.

FIG. 2 is a not to scale top view of the laser scalpel of FIG. 1.

STRUCTURE AND USE

Figure 3A:
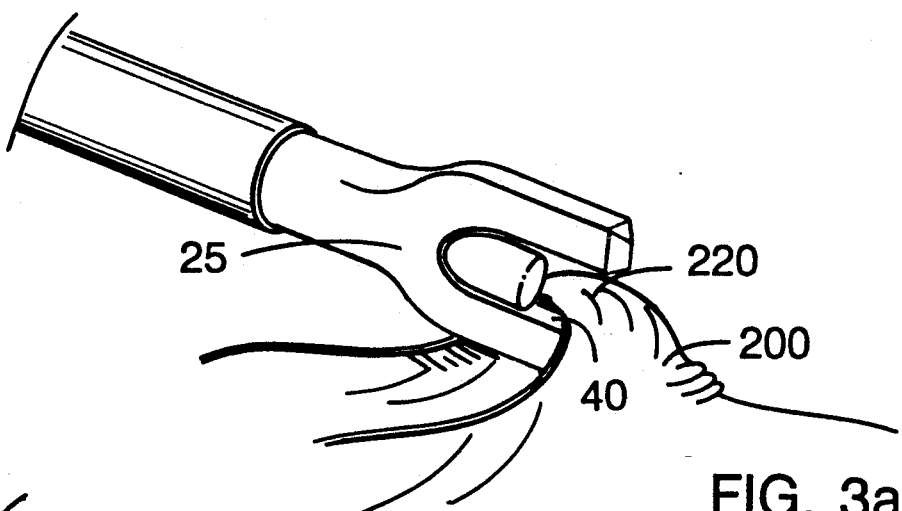
FIG. 3 is a not to scale diagram of a method of surgical unzipping.

FIGS. 1 and 2 show laser scalpel 10 including hollow handpiece or tubular conduit 15, headpiece 20, primary dissection prong 25 with lateral surface 30, outer surface 35, inner surface 40, and distal tip 45, auxiliary dissecting prong 50 with lateral surface 55, outer surface 60, inner surface 65, and distal tip 70, laser beam transmitting filament 75 with distal tip 80 and proximal end 85, locking nut 90, irrigation/aspiration connector 95, irrigation/aspiration connector lumen 100, irrigation/aspiration channel 105, and irrigation/aspiration port 110.

Laser filament 75 passes through locking nut 90, handpiece 15, and headpiece 20 to emerge disposed between primary dissecting prong 25 and auxiliary dissection prong 50. Locking nut 90 holds filament 75 in place but can be loosened to allow adjustment of the position of laser filament distal tip 80 relative to primary dissection prong distal tip 70. The appropriate placement of distal tip 80 of laser filament 75 in relation to distal tip 45 and distal tip 70 of the dissecting prongs for a given surgical procedure is determined by methods known to those skilled in the art. In many applications it is desirable that distal tip 45 of primary prong 25 extends beyond distal tip 80 of laser filament 75. Locking nut 90 and irrigation/ aspiration connector 95 can be fabricated from a standard 2-way connector by methods known to those skilled in the art. The lumen of irrigation/aspiration connector 100 is continuous with the interior of handpiece 15 and irrigation channel 105, allowing aspiration of unwanted material from the surgical field or the introduction of irrigating solution (or other solutions) to the surgical field through irrigation-/aspiration port 110. Alternatively, the device can include separate lumens and channels for irrigation and aspiration. For example, an irrigating fluid could be conducted to the surgical field through one dissecting prong and material in the surgical field aspirated through a second dissecting prong. Alternatively, both passages could pass through a single dissecting prong. The handpiece and headpiece could have multiple lumens or channels to carry irrigating fluid to the surgical field or to aspirate the surgical field.

Handpiece or tubular conduit 15 can be thermally insulated to protect the surgeon and patient from heat buildup. (The handpiece may also be electrically insulated). The laser conducting filament can be any flexible filament capable of transmitting laser emissions, e.g., a 600 $\mu$m quartz filament. The dissecting and auxiliary dissecting prongs can be fabricated from any material that can withstand the heat of the laser, e.g., a refractory noble metal, e.g., rhodium, palladium, platinum, or platinum-iridium alloys, stainless steel, copper, platinum coated copper, palladium coated copper, or ceramic materials, e.g., alumina nitride, silicon carbide or sapphire. In applications where it is desirable that the prongs be hot, e.g., to assist in dissections, a material which is a less efficient conductor of heat, e.g., steel, should be used. If heat buildup in the prongs is undesirable the prongs can be cooled by providing coolant channels in the interior of the prongs and circulating coolant, e.g., water or refrigerant, through the channels. Control of the prong temperature can be regulated by a sensor, e.g., a thermocouple, which controls the flow of coolant. The flow of irrigating solution, or the flow of aspiration material, can also be used to control temperature.

The various edges of the primary and auxiliary dissecting prongs may be sharp or blunt, or otherwise formed as required by a particular surgical procedure. A material such as teflon may help prevent sticking of tissue to the scalpel and may be applied, e.g., by spraying, to the instrument. Gold plating (with or without an additional layer of Paralyne (Union Carbide)) can be applied to the dissecting elements to reduce sticking. In use, the proximal end of the filament 75 is connected to a laser source, e.g., a Nd:YAG, KTP, or Holmium:YAG laser source, and irrigation/aspiration connector 95 is connected to a source that can provide irrigating solution and/or vacuum.

The laser scalpel of FIGS. 1 and 2 is particularly useful in procedures where both sharp dissection, e.g., cutting, as with a standard steel scalpel or a laser beam, and blunt dissection, e.g., the separation of one object from another by manipulation of blunt instruments, e.g., fingers, the side and blunt edge of a steel scalpel blade, or the dissecting prong of the device in FIGS. 1 and 2, are required, for example, where a first structure is blunt dissected away from a second structure and the first structure then cut by sharp incision. An example of such a procedure is the removal or opening (unzipping) of a membrane which covers an organ or other underlying surface or object, e.g., where the membrane is opened followed by incision of the membrane with the cutting and coagulating element.

Figure 3B:
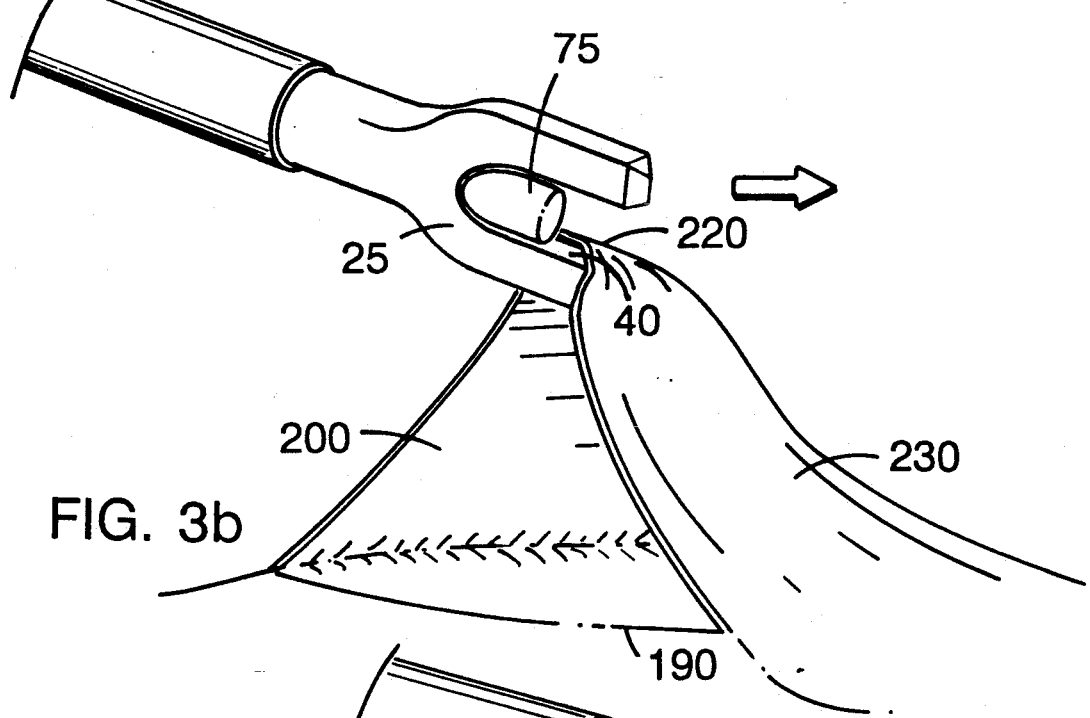
Figure 3C:
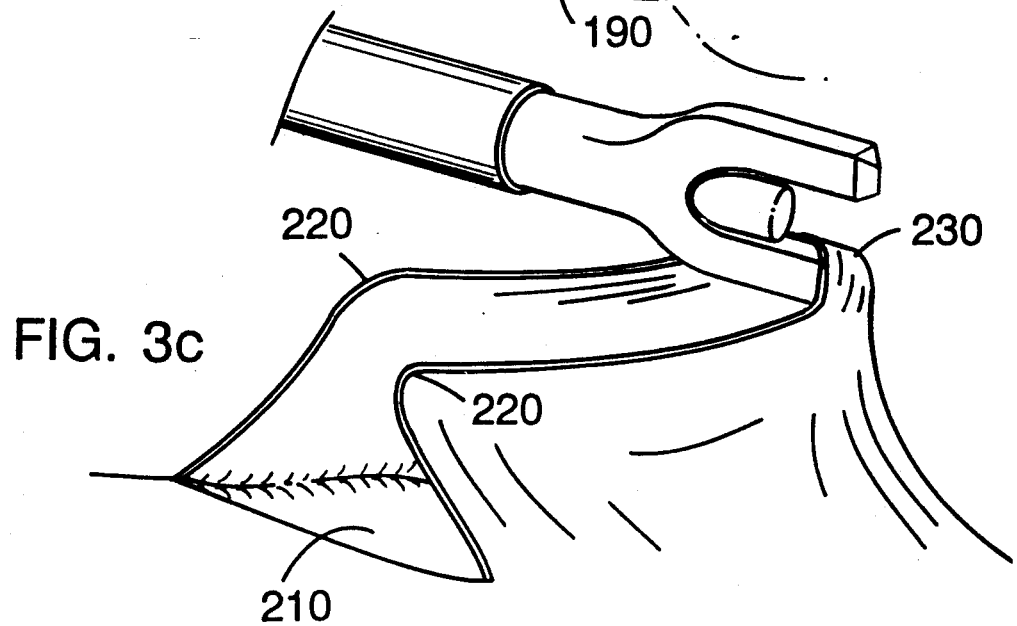

The use of the laser scalpel of FIG. 1 and 2 to unzip a membrane is shown in FIG. 3. In FIGS. 3a and 3b, primary dissecting prong 25 of the laser scalpel is used to hook and lift membrane 200 and make initial cut 190 in the membrane. In FIG. 3b, membrane 200 is separated from underlying structure 210 using primary dissecting prong 25 and inner surface 40 to hook the membrane at position 220 on initial cut 190 and lift it away from underlying structure 210. While lifting the membrane away from the underlying structure the surgeon moves the laser scalpel in the direction indicated by the arrow in FIG. 3b. As the laser scalpel moves in the direction shown, uncut membrane comes into close proximity or contact with laser filament 75 and is cut, as shown in FIG. 3c. Continuing travel in the direction shown extends the cut to new point 230 on the membrane. As long as the surgeon continues this motion the membrane is supported by dissecting prong 25 and is fed over inner surface 40 to laser filament 75 and is cut.

Animal Studies: Laparoscopic Laser Cholecystectomy

The coagulating scalpels of the invention are particularly useful in endoscopic, e.g., laparoscopic surgical procedures. The coagulating scalpels of the invention can be made suitable for use in endoscopic procedures by constructing them from miniaturized and/or flexible components, by methods known to those skilled in the art.

A laser scalpel similar to that shown in FIGS. 1 and 2, but constructed from miniaturized and flexible components so that it could be passed through a laparoscope, was used to perform a laparoscopic laser cholecystectomy on a pig. The distal end of the laser scalpel was configured essentially as shown in FIGS. 1 and 2, with a 600 $\mu$m flexible quartz laser transmitting filament disposed between two dissecting prongs. The tips of the primary dissecting and auxiliary dissecting prongs extended about 2 mm beyond the tip of the laser filament. The distance between the laser filament and the dissecting prong was about 300 $\mu$m and the distance between the laser filament and the auxiliary dissecting prong was about 300 $\mu$m. The structure formed by the two prongs was flattened and spatulate, as shown in FIGS. 1 and 2. Taken together the dissecting prongs formed a structure about 80-100 mm long, about 2 mm thick, and about 4.5 mm wide (where width is the distance from the outside face of the auxiliary prong to the outside face of the primary prong). The length of the tubular conduit was about 15-30 cm.

The laser scalpel was passed through a 5 mm instrument port of an endoscope and the proximal end of the laser filament connected to a continuous wave Nd:YAG laser with an output of 20 watts.

During laparoscopic cholecystectomy the gallbladder is usually dissected from the liver with an electrocautery device or a laser. The spatulate form of the distal end of the laser scalpel simplified dissection of the gallbladder and the fork formed by the primary dissecting prong and the laser filament simplified hooking, lifting, and cutting (unzipping) the gallbladder peritoneum. In addition to simplifying and speeding dissections, the laser scalpel of the invention produced little thermal damage and gave a clean plane of dissection, as compared to that produced by electrocautery. The ability to irrigate the field of dissection was useful in keeping the field clean and unobstructed and in cooling the dissecting prongs.

Human Trials

A laser scalpel similar to the one described above was used to perform 15 human laparoscopic gynecologic procedures at Massachusetts General Hospital. The surgeries were performed by one reproductive surgeon (KI) and consisted of 2 ovarian cystectomies, 1 paraovarian cystectomy, 1 tuboplasty and 11 adhesiolysis. A KTP 532 nm laser (Laserscope) was used in a continuous mode at 7 watts power. Laser energy was transmitted via a 600 micron quartz optical fiber. By placing the tissue to by lysed under tension, the device enabled the surgeon to perform the above procedures in a more rapid and hemostatic fashion than would be possible using conventional bare fiber techniques.

Other Embodiments

Other embodiments are within the following claims, for example, coagulating scalpels of the invention can be used in gynecological, cardiothoracic, urological, gastrointestinal, opthalmic, or ENT (ear, nose, and throat) procedures and particularly in endoscopic variants of surgical procedures. Embodiments of the invention are useful in separating adhesions, e.g., in membrane separations, e.g., in establishing a surgical plane between adjacent membranes. The size, shape, and placement of the dissecting prong or prongs can be varied to suit a given surgical procedure, e.g., the dissecting prong or prongs can be elongate, shortened, hooked, curved, bulbous, blunt, sharp, smooth, or serrated. The handpiece can have a variety of shapes and lengths, it can possess hollow joints, and it can be flexible or rigid, as required by a particular application. The tip of the cutting and coagulating element can have any suitable shape, e.g., the distal face can be flat, or the distal end of the cutting and coagulating element can be bulbous or spherical.

The device can be miniaturized and otherwise adapted for endoscopic use.

The device can be fitted with joints or other modifications known to those skilled in the art to allow articulation as desired by the surgeon, e.g., the device may be hinged, e.g., just proximal to the cutting and coagulating element and dissecting means, to allow side-to-side manipulation, e.g., to change the angle between the long axis of the hand piece and the long axis of the dissecting means. Alternatively, a segment of the device between the dissecting element and handset can be made of a coiled member, or of flexible plastic, to allow deflection of the tip, in essentially any direction, by central wires running from the dissecting element to the proximal end of the device. Once a new deflection is made it can be locked in place by securing the control wire. Alternatively, the flexible segment could be made of a material which retains the new shape into which it is deflected. The cutting and coagulating element and/or the dissecting element can be mounted on the hand piece such that they can be rotated (along their long axis) with respect to the hand piece.

Figure 4:
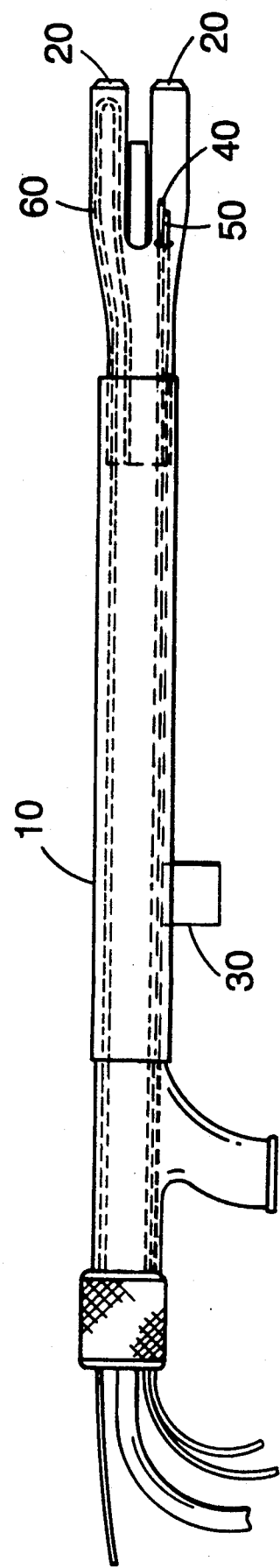
FIG. 4 is a not to scale diagram of an alternative embodiment of a laser scalpel.

The device may also include other surgical tools. For example, as shown in FIG. 4, devices of the invention 10 can include an integral electrocautery element (separate from the cutting and coagulating means) to allow the surgeon to switch to conventional electrocautery without changing surgical instruments. In this embodiment, current is supplied to the dissecting element 20 or elements e.g., by a power lead 30 attached to a point on the handpiece which is electrically connected to the dissecting element or elements. (The patient is normally connected to ground). In this embodiment the dissecting elements can thus be used as an electrocautery element, independently or in conjunction with other capabilities of the device. For example, crude manipulation can be performed with the electrocautery capability of the dissecting elements and finer manipulations can be performed with the cutting and coagulating element.

The device of the invention can also include a loop or snare for snaring (at the distal end of the instrument) and securing a portion of tissue, e.g., a polyp; a hydrodissecting element; and a channel or other element to allow the device to be negotiated over a guide wire. Devices of the invention can also include means for illuminating and viewing the surgical field. For example, as shown in FIG. 4, the device 10 can include a conventional optical fiber 40 for transmitting a view of the surgical field to the operator and an optical fiber 50 for illuminating the surgical field. The device in FIG. 4 also includes a cooling channel 60 in a dissecting element.

The laser scalpels of the invention are particularly useful as surgical scalpels. Some devices and methods of the invention may, however, find application in other areas.

What is claimed is:

1. A coagulating scalpel the distal end of which comprises
   a first dissecting element,
   a second dissecting element, and
   a cutting and coagulating element,
   said first dissecting element having a distal end, a longitudinal axis, an inner surface which faces a gap between said first dissection element and said second dissecting element and which is adapted to permit substantially free passage of tissue over said surface, and an outer surface which does not face a gap between said first dissecting element and said second dissecting element,
   said second dissecting element having a longitudinal axis, an inner surface which faces a gap between said first dissecting element and said second dissecting element and, and an outer surface which does not face a gap between said first dissecting element and said second dissecting element, and
   said cutting and coagulating element comprising an optical filament having a distal end, a focal point, a longitudinal axis, and a portion that lies adjacent said dissecting elements,
   said optical fiber being positioned in said gap between said first and said second dissecting elements, said focal point of said optical filament being proximal to said distal end of said first dissecting element, and said longitudinal axes of said first and second dissecting elements and said longitudinal axis of said portion of said optical fiber that lies adjacent said dissecting elements being essentially parallel.

2. The coagulating scalpel of claim 1, further comprising means for adjusting the position of the distal end of said cutting and coagulating element relative to the distal end of said first dissecting element.

3. The coagulating scalpel of claim 1, wherein said distal end of one of said dissecting elements is flush with the distal end of said optical fiber.

4. The coagulating scalpel of claim 1, wherein said distal end of said optical fiber extends beyond said distal end of one of said dissecting elements.

5. The coagulating scalpel of claim 2, wherein said distal end of both of said dissecting elements extends beyond the distal end of said optical fiber.

6. The coagulating scalpel of claim 5, wherein the distal end of one or both of said dissecting elements extends no more than approximately 30 millimeters beyond the distal end of the cutting and coagulating means.

7. The coagulating scalpel of claim 5, wherein the distal end of one or both of said dissecting elements extends no more than approximately 15 millimeters beyond the distal end of the cutting and coagulating means.

8. The coagulating scalpel of claim 5, wherein the distal end of one or both of said dissecting elements extends no more than approximately 10 millimeters beyond the distal end of the cutting and coagulating means.

9. The coagulating scalpel of claim 5, wherein the distal end of one or both of said dissecting elements extends no more than approximately 5 millimeters beyond the distal end of the cutting and coagulating means.

10. The coagulating scalpel of claim 5, wherein the distal end of one or both of said dissecting elements extends no more than approximately 1 millimeter beyond the distal end of the cutting and coagulating means.

11. The coagulating scalpel of claim 5, wherein the distal end of one or both of said dissecting elements extends no more than approximately 7 millimeters beyond the distal end of the cutting and coagulating means.

12. The coagulating scalpel of claim 1, wherein the lateral distance between the outer surface said first dissecting element and the outer surface of said second dissecting element is less than about 10 millimeters.

13. The coagulating scalpel of claim 1, wherein the lateral distance between the outer surface said first dissecting element and the outer surface of said second dissecting element is less than about 4 millimeters.

14. The coagulating scalpel of claim 1, wherein the lateral distance between the outer surface said first dissecting element and the outer surface of said second dissecting element is less than about 2 millimeters.

15. The coagulating scalpel of claim 1, wherein the lateral distance between the outer surface said first dissecting element and the outer surface of said second dissecting element is less than about 0.4 millimeters.

16. The coagulating scalpel of claim 1, wherein the lateral distance of a gap between said first and said second dissecting element is less than about 0.075 millimeters.

17. The coagulating scalpel of claim 1, wherein the lateral distance of a gap between said first and said second dissecting element is less than about 0.4 millimeters.

18. The coagulating scalpel of claim 1, wherein the lateral distance of a gap between said first and said second dissecting element is less than about 0.8 millimeters.

19. The coagulating scalpel of claim 1, wherein the lateral distance of a gap between said first and said second dissecting element is less than about 1.5.

20. The coagulating scalpel of claim 1, wherein the lateral distance of a gap between said first and said second dissecting element is less than about 4 millimeters.

21. The coagulating scalpel of claim 1, wherein the lateral distance of a gap between said first and said second dissecting element is less than about 8 millimeters.

22. The coagulating scalpel of claim 1, wherein said cutting and coagulating element and said dissecting elements are disposed such that a line coaxial with the longitudinal axis of said cutting and coagulating element and extending beyond the distal tip of said cutting and coagulating element does not intersect either of said dissecting elements.

23. The coagulating scalpel of claim 1, wherein said cutting and coagulating element is an optical filament capable of transmitting laser light.

24. The coagulating scalpel of claim 1, wherein there is a gap between said cutting and coagulating element and said dissecting element.

25. The coagulating scalpel of claim 1, wherein said dissecting element comprises a sharp edge.

26. The coagulating scalpel of claim 1, wherein said dissecting element comprises a blunt edge.

27. The coagulating scalpel of claim 1, further surprising means for cooling said dissecting element.

28. The coagulating scalpel of claim 1, further comprising means for removing unwanted material from the area of cutting and coagulating.

29. The coagulating scalpel of claim 1, further comprising means for irrigating the area of cutting and coagulating.

30. The coagulating scalpel of claim 1, wherein said dissecting forks can be used as electrocautery elements.

31. The coagulating scalpel of claim 1, adapted for endoscopic use.

32. A surgical method for cutting a biological structure comprising,
providing a coagulating scalpel the distal end of which comprises a first dissecting element having a distal end, a longitudinal axis, an inner surface which is adapted to permit substantially free passage of tissue over said surface, and an outer surface, a second dissecting element having a longitudinal axis, an inner surface, and an outer surface, and a cutting and coagulating element comprising an optical filament having a distal end, a focal point, a longitudinal axis, and a portion that lies adjacent said dissecting elements, said optical fiber being positioned in a gap between said first and said second dissecting elements, said focal point of said optical filament being proximal to said distal end of said first dissecting element, and said longitudinal axes of said first and second dissecting elements and said longitudinal axis of said portion of said optical fiber that lies adjacent said dissecting elements being essentially parallel,
engaging all or a portion of said structure in the gap between said first and said second dissecting elements,
moving said scalpel to impart mechanical force to said structure, and
activating said cutting and coagulating element to cut said structure.

33. The surgical method of claim 32, further comprising moving said scalpel in the direction in which said first structure is to be cut to impart said mechanical force.

34. The surgical method of claim 32, wherein said activation of said cutting and coagulating element and said movement are performed simultaneously, thereby combining the action of said cutting and coagulating element with said mechanical force imparted by movement of said scalpel to cut tissue.

35. The surgical method of claim 34, wherein a combination of heat and mechanical force cut said structure.

36. The surgical method of claim 32, wherein said structure is a planar structure.

37. The surgical method of claim 36, wherein said planar structure is a membrane.

38. The method of claim 32, further characterized in that it is performed endoscopically.

39. The method of claim 32, wherein said first structure is a membrane adjacent the gallbladder.

40. The method of claim 1, wherein less than 10 watts of power are supplied to said cutting and coagulating element.

41. The method of claim 1, wherein less than 8 watts of power are supplied to said cutting and coagulating element.

42. The method of claim 1, wherein less than 6 watts of power are supplied to said cutting and coagulating element.

* * * * *

UNITED STATES PATENT AND TRADEMARK OFFICE
CERTIFICATE OF CORRECTION

PATENT NO. : 5,254,115

DATED : October 19, 1993

INVENTOR(S) : Krishna M. Bhatta and Thomas E. Haw

It is certified that error appears in the above-indentified patent and that said Letters Patent is hereby corrected as shown below:

On the title page, item [56], under "OTHER PUBLICATIONS", please add the following:

Joffe, Lasers in Surgery and Medicine, Vol. 6, pp. 155-157, 1986;

Kim et al., Neurosurgery, Vol. 21, pp. 858-860, 1987;

Miller et al., Arthroscopy: The Journal of Arthroscopic and Related Surgery, Vol. 5, pp. 245-253, 1989;

Col. 3, line 45, replace "distal tip of the can be adjusted." to --distal tip can be adjusted--;

Col. 4, line 34, replace "an movement" with --and movement--;

UNITED STATES PATENT AND TRADEMARK OFFICE
CERTIFICATE OF CORRECTION

PATENT NO.   : 5,254,115
DATED        : October 19, 1993
INVENTOR(S)  : Krishna M. Bhatta and Thomas E. Haw It is certified that error appears in the above-indentified patent and that said Letters Patent is hereby corrected as shown below:

Col. 6, line 46, replace "seperate" with --separate--.

Col. 7, line 42, replace "conventiional" with --conventional--.

Col. 12, claim 1, line 26, replace "dissection" with --dissecting--.

Col. 14, claim 27, line 15, replace "surprising" with --comprising--.

Signed and Sealed this

Nineteenth Day of July, 1994

Attest:

BRUCE LEHMAN

Attesting Officer        Commissioner of Patents and Trademarks